US005770705A

United States Patent [19]
Shanbrom

[11] Patent Number: 5,770,705
[45] Date of Patent: Jun. 23, 1998

[54] METHOD FOR RECOVERING PROTEINS FROM PLASMA USING INSOLUBLE, WATER-ABSORBING MATERIAL

[75] Inventor: Edward Shanbrom, Santa Ana, Calif.

[73] Assignee: Shanbrom Technologies LLC, Ojai, Calif.

[21] Appl. No.: 742,510

[22] Filed: Nov. 1, 1996

[51] Int. Cl.$^6$ ............................... A23J 1/00; C07K 1/00; A61K 35/14
[52] U.S. Cl. .................... 530/421; 530/380; 530/381; 530/382; 530/383; 530/384
[58] Field of Search .................................. 530/383, 412, 530/418, 419, 421, 420; 210/689; 514/12

[56] References Cited

U.S. PATENT DOCUMENTS

| | | |
|---|---|---|
| 3,560,475 | 2/1971 | Fekete et al. . |
| 3,631,018 | 12/1971 | Shanbrom et al. . |
| 3,682,881 | 8/1972 | Fekete et al. . |
| 4,069,216 | 1/1978 | Shanbrom . |
| 4,093,608 | 6/1978 | Iga et al. ............................. 260/112 B |
| 4,305,871 | 12/1981 | Shanbrom . |
| 4,555,344 | 11/1985 | Cussler ..................................... 210/634 |
| 5,696,236 | 12/1997 | Omar et al. .............................. 530/380 |

Primary Examiner—Sandra E. Saucier
Attorney, Agent, or Firm—Graham & James LLP

[57] ABSTRACT

Enhanced production of cryoprecipitate is produced by dehydrating an individual unit of plasma prior to a low temperature step used to produce cryoprecipitate. This dehydration is accomplished either by placing a water absorbing material within a blood bag so that plasma occupying the bag will become dehydrated or by placing the water absorbing material within a cartridge so that plasma becomes dehydrated upon flowing through the cartridge. The preferred water-absorbing material is a cross-linked chromatographic gel having pores too small to admit clotting proteins, but large enough to admit water molecules. Suitable gels are made from carbohydrates or polyacrylamide. Carbohydrate gels such as Sephadex®, produced by Pharmacia-Upjohn, are particularly preferred in the present invention. An alternative embodiment of the invention replaces the simple water-absorbing gel with one that also has ion exchange capabilities, such as DEAE (diethy-aminoethyl) Sephadex which has an especial affinity for a number of blood clotting factors collectively known as the prothrombin complex. Following the dehydration step the DEAE Sephadex is eluted to produce prothrombin complex.

13 Claims, 1 Drawing Sheet

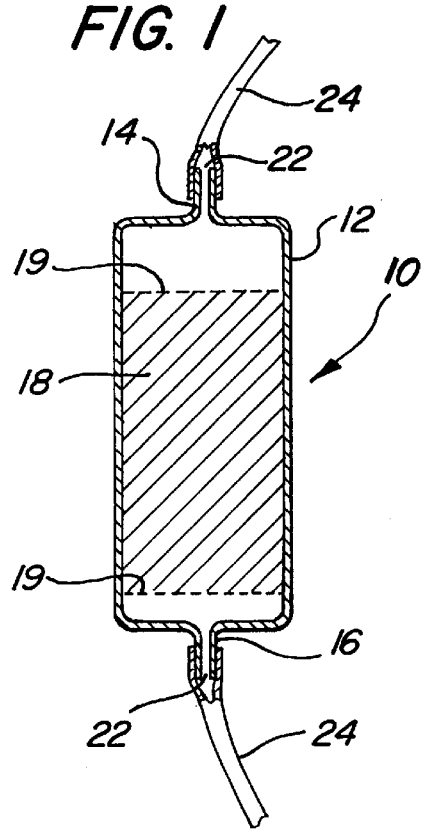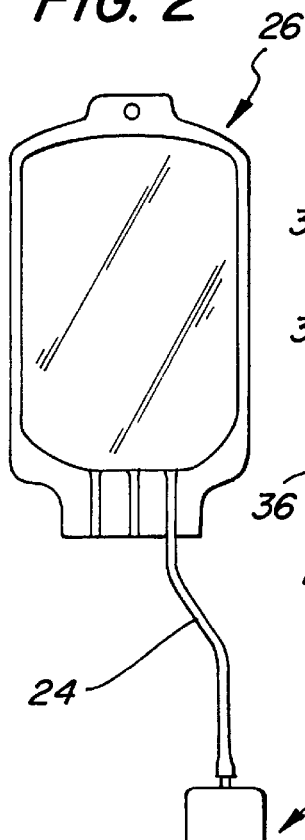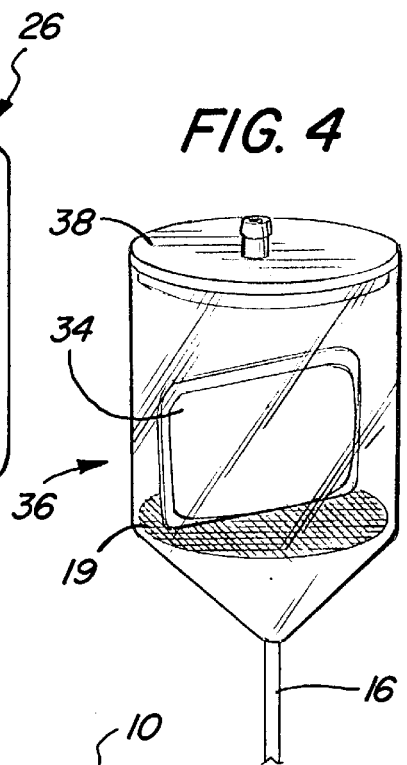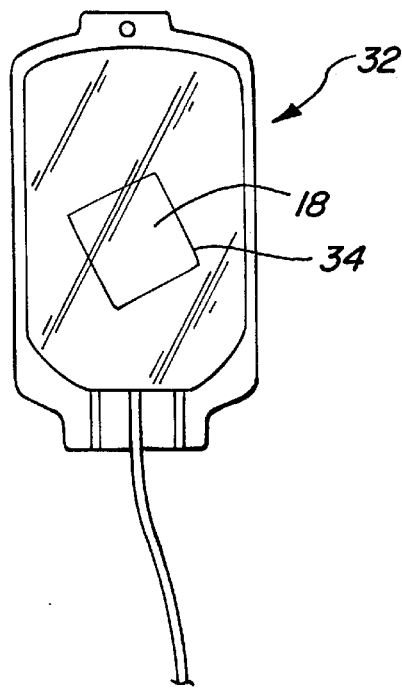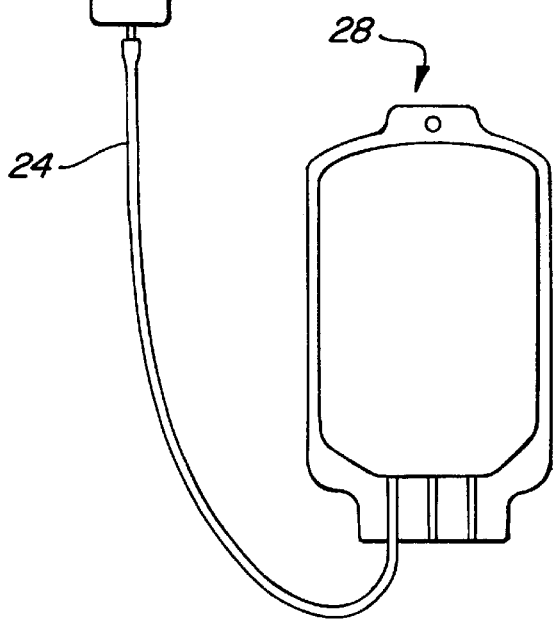

METHOD FOR RECOVERING PROTEINS FROM PLASMA USING INSOLUBLE, WATER-ABSORBING MATERIAL

BACKGROUND OF THE INVENTION

1. Field of the Invention

The present invention relates to an improved method for producing antihemophilia factors or concentrates from blood and, more particularly, to a method and apparatus that allows ready and efficient preparation of clotting factors from blood from single donors.

2. Description of Related Art

Individuals with one of a series of genetic abnormalities affecting the proteins responsible for blood clotting are afflicted with a disease in which the blood fails to clot normally, subjecting the individual to the danger of uncontrolled bleeding. For many years this condition has been treated by administering concentrates of the missing or defective proteins. At this time there is still no cost effective method of artificially manufacturing each of these proteins, so they must be purified from donated human blood. Although there have been methods for preparing these concentrates from single units of donated blood, these methods have generally been less efficient than bulk preparation from pooled blood. At this time the vast majority of antihemophilia factor (AHF, also known as Factor VIII), and other blood factors are prepared from pooled plasma. Because a hemophiliac requires treatment for the whole of his lifetime, he (the majority of hemophiliacs are male) necessarily receives blood products from a large number of donors.

The presence of AIDS (Acquired IimmunoDifficiency Syndrome) virus in the blood supply means that many hemophiliacs have become infected with this terrible disease. Although tests to screen out AIDS-tainted blood have been improved, some infected blood does slip by. Since hemophiliacs are exposed to a large number of donors, they are at heightened risk. Even if the AIDS problem is solved, the danger of other blood-borne diseases, such as the various types of hepatitis and other infectious agents, makes it desirable to reduce the use of pooled-blood in preparing blood concentrates. If each hemophiliac received AHF purified from only a single, or a small number of donors, the dangers of blood borne infection would be substantially reduced.

The basic methods for preparing these clotting concentrates from blood has not changed greatly over the last few decades. Generally, AHF is derived from pooled plasma by a cryoprecipitation step. Various additives such as ethanol or polyethylene glycol are usually added to enhance the efficiency of the cryoprecipitation step. Following cryoprecipitation, the partially purified AHF is further purified by additional precipitation steps or by chromatographic methods, most recently utilizing monoclonal antibodies. For additional information on the basic techniques of AHF purification and the history of the development of these methods, the reader is directed to U.S. Pat. Nos. 3,560,475. 3,631,018, 3,682,881, 4,069,216, and 4,305,871, by the present inventor, and the references cited therein.

OBJECTS AND SUMMARY OF THE INVENTION

It is an object of the present invention to provide a method whereby excellent yields of AHF as well as fibrinogen, fibronectin and "fibrin glue" or "fibrin sealant" can be readily produced from individual units of blood;

It is an additional object of the present invention to provide a simple to use device to practice the method of the present invention, the device being a modification to or an add on to a traditional blood bag; and It is still a f further object of the present invention to provide a method and device for producing prothrombin complex from the same plasma that is used to produce AHF.

These and additional objects are met by a method of dehydrating an individual unit of plasma prior to a low temperature step used to produce cryoprecipitate. This dehydration is accomplished either by placing a water absorbing material within a blood bag so that plasma occupying the bag will become dehydrated or by placing the water absorbing material within a cartridge so that plasma becomes dehydrated upon passing through the cartridge. Generally, the preferred water-absorbing material is a chromatographic gel having pores too small to admit clotting proteins, but large enough to admit water molecules. Suitable gels are made from carbohydrates or polyacrylamide and are commonly used in various chromatographic procedures. Carbohydrate gels such as Sephadex®, produced by Pharmacia-Upjohn, are particularly preferred in the present invention. Other dehydrating matrices like starch, carboxymethylcellulose, polyethylene glycol (i.e., Aquacides, Calbiochem) or gelatin could be utilized in the present invention, but are generally not preferred because of the significant possibility that such materials would absorb significant quantities of clotting proteins as well as water unless used with a dialysis membrane. An alternative embodiment of the invention replaces the simple water-absorbing gel with one that also has ion exchange capabilities, such as DEAE (diethy-aminoethyl) Sephadex, which has an especial affinity for a number of blood clotting factors collectively known as the prothrombin complex. Following the dehydration step the DEAE Sephadex is eluted to produce prothrombin complex.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 shows a cartridge used in the practice of the present invention;

FIG. 2 shows the device of FIG. 1 connected between two blood bags;

FIG. 3 shows an alternate embodiment where the dehydrating material is enclosed as a permeable packet within the blood bag; and FIG. 4 shows the use of a wide column to elute the prothrombin complex from the packet of FIG. 3.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method and a device for efficiently producing AHF, and other blood proteins, from single units of plasma.

The traditional method for producing AHF, as well as the presently used methods, operate because key plasma proteins precipitate (form cryoprecipitate) from solution at low temperatures when they are sufficiently concentrated. When a protein solution is frozen, ice crystals form and the proteins which are excluded from the crystals become increasingly concentrated. Depending on the particular proteins, the proteins may actually fall out of solution, i.e., form a precipitate, if the protein more readily interacts with itself or other proteins than with water. This process may denature the proteins (make them irreversibly insoluble), so it is usual to freeze protein solutions rapidly and to a low temperature (i.e., −20° C. or lower) to minimize the formation of ice crystals and to prevent the growth of those crystals that do form. This is done to limit protein denaturation on ice crystal surfaces. Even when freezing is carried out with great care, ice crystals may cause "activation" of the prothrombin complex, resulting in spontaneous clot formation.

The first step in the typical procedure for producing plasma cryoprecipitate is to centrifuge whole blood to separate the plasma from the red blood cells. This procedure is well known in the art and is often accomplished in special centrifuges that hold individual blood bags so that the plasma/red cell separation occurs without even opening the blood bag. Obviously, bulk methods can also be used, but the present invention is particularly aimed towards purifying individual units of blood to minimize the number of donors to which any one patient becomes exposed. Following the centrifugation it is common practice to express the supernatant plasma into a "satellite" blood bag for further processing. Once the plasma is separated, the typical procedure is to rapidly freeze the plasma and to then slowly thaw the frozen plasma at 4° C., during which thawing the AHF and other proteins form a cryoprecipitate which can be readily harvested by filtration or centrifugation. This cryoprecipitate is not irreversibly insolubilized and can be readily extracted (redissolved) in a low ionic strength buffer, as is well known in the art.

Cryoprecipitation results when the removal of water from the immediate vicinity of the protein molecules causes the proteins to preferentially associate with each other rather than with water. This "removal" of water may be accomplished or enhanced through the use of additives which "tie up" the water and cause it to interact less with the proteins. These additive substances can be any of a number of hydrophilic materials such as ethanol, polyethylene glycol, heparin, and Pluonic® polyol polymers. These and other materials used to increase the yield of cryoprecipitate generally operate to decrease the effective activity of water in the mixture. That is, the water molecules preferentially interact with the added hydrophilic material instead of with the proteins. This permits the proteins to interact with each other and, therefore, precipitate from solution. Lowering the temperature also decreases the activity of water, allowing protein-protein interactions to predominate.

The hydrophilic additives just mentioned have the advantage of being relatively inexpensive and easy to use. However, their use usually necessitates additional washing steps to ensure that the additives are not carried over into the final AHF product. Also, having to add hydrophilic materials necessitates additional manipulation of the plasma. This may not be a significant drawback in large bulk preparations where many units of plasma from a number or donors are pooled. However, such additional manipulation of the plasma is not favored in the current invention, which uses single units of plasma and seeks to limit labor and worker contact with the plasma. The present inventor has realized that an additional way to limit water activity and enhance formation of the cryoprecipitate is simply to decrease the actual amount of water in the solution. This is accomplished by treating the plasma with a dehydrating material that absorbs water but not protein from the plasma. Many different dehydrating materials are adaptable to the present invention. The key criteria are that the material be insoluble and that it minimally denatures or absorbs the plasma proteins. A large number of polymeric materials such as polymerized polyvinyl alcohol-acetal, carbohydrate gels, and hydrophilic organic polymers (i.e., polyacrylamide) are suitable for the present invention. Other dehydrating agents such as carboxymethylcellulose can be used with the addition of a semipermeable membrane to avoid absorption or protein. However, this membrane adds complexity and generally slows the dehydration.

The presently preferred dehydrating material is Sephadex (G-25 to G-100). Other similar Sephadex products, as well as other cross-linked polymeric material with similar properties can be used. The Sephadex materials consists of small beads of cross-linked dextrans (glucose polymers). The material is so constructed that the pores between the cross-linked carbohydrate molecules are too small to admit any but the smallest of proteins. However, water and small solutes readily penetrate these pores where the water becomes trapped by interacting with (swelling) the carbohydrate. Such materials are widely used in protein biochemistry in desalting and chromatographically fractionating protein or other mixtures of macromolecules. However, to the knowledge of the present inventor, they have not been directly applied to the production of AHF from single units of plasma. Other dehydrating methods such as ultrafiltration could conceivably be used, but such methods do not lend themselves as simply to the disposable apparatuses that are preferred with the present invention.

A significant advantage of using dehydrating agents is that useful amounts of cryoprecipitate can be formed upon mere chilling (i.e. to 4° C.) rather than requiring actual freezing and thawing of the dehydrated plasma, thereby allowing one to obtain clotting factors that have not been activated by contact with ice crystals. Of course, after a first quantity of cryoprecipitate is formed by chilling, the plasma can then be subjected to freezing and thawing to yield a second quantity of cryoprecipitate.

Different types of Sephadex swell at different rates. To evaluate these differences 1 gram aliquots of four different types of Sephadex were imbibed with 30 ml distilled water each and the swelling was observed and measured. Table 1 shows the final volume of fully swelled gels after 24 hours.

TABLE 1

| | |
|---|---|
| Sephadex G-25 | 5.0 ml |
| Sephadex G-75 | 13.0 ml |
| Sephadex L-20 | 4.0 ml |
| Sephadex L-60 | 12.0 ml |

These results show that the "higher number" gels swell to a much greater extent (take up greater amounts of water). This is consistent with the fact that these gels are less tightly cross-linked and have larger pore sizes. Essentially, higher number gels are preferred for dehydration in the current invention because they take up greater amounts of water. However, attention must be paid to the fact that these same gels have larger pores that also take in higher molecular weight proteins. Thus, effectiveness at dehydration must be balanced against possible loss of protein within the gel matrix in selecting the ideal gels for use in the present invention. Generally, G-75 gel does not absorb an excessive amount of protein (as compared to its favorable dehydrating properties). More open gels, i.e., G-100 and above, take in more and more protein and are less highly favored.

EXAMPLE 1

This example utilizes a dehydrating cartridge 10 such as that shown in FIG. 1. This cartridge has a generally cylindrical hollow body 12 with an inlet port 14 and an outlet port 16. The hollow body is filled with sufficient Sephadex gel 18 to efficiently dehydrate a single unit (about 500 milliliters) of plasma. Frit 19 (often just a disc of fine nylon mesh or similar material) is provided to keep the Sephadex from escaping through the outlet port 16. A second frit 19' can also be provided to avoid escape through the inlet port 14. It has been found that optimum results are obtained if the plasma is dehydrated by at least about 50%; that is, if 100 ml of plasma are reduced to 50 ml, but any removal of water will result in an increase in the amount of precipitated protein. The inlet 14 and outlet ports 16 are equipped with standard fittings 22 so the cartridge 10 can be readily connected, with flexible tubing 24, between a first blood bag 26 and a second blood bag 28 (see FIG. 2). Depending on the precise type of blood bags used, the tubing may come preattached to the blood bag, or if not so attached may come preattached to the cartridge. Alternatively, separate lengths of tubing can be employed.

Those familiar with the use of Sephadex and similar materials will be aware that they swell considerably upon imbibing water. Therefore, it is essential to allow sufficient head room in the cartridge 10 to accommodate this swelling. The amount of volume needed depends on the type of Sephadex selected with the higher number materials (i.e., G-100 as opposed to G-25 swelling to a much greater extent, see Table 1). If an inlet frit 19' is used, that frit 19' must be capable of deforming or changing its position as the Sephadex gel swells.

In use, the plasma flows from the first blood bag 26, through the cartridge 10 and into the second blood bag 28. Usually, the flow is simply caused by gravity. Alternatively, the plasma flow can be aided by any of a number of methods that avoid opening the bag and risking potential contamination of personnel—methods such as a peristaltic pump system applied to the tubing 24 or some sort of pressure cuff or chamber applied to the blood bag 26 are appropriate. The critical factor is that the plasma flow rate through the cartridge be sufficiently slow that adequate dehydration occurs. The degree of dehydration achieved is a product of flow rate and of the ratio between the total plasma volume and the volume of the Sephadex. A slower flow rate and/or an increased volume of available Sephadex will lead to a greater level of dehydration. However, a certain amount of plasma is permanently retained by the Sephadex so that the larger the volume of Sephadex, the larger the amount of plasma lost. Also, if dehydration is excessive, protein may precipitate within the cartridge and be lost.

After the plasma has all passed through the cartridge, it is advantageous to wait an additional time (a few minutes) for residual plasma to drain from the cartridge. It is also possible to express additional retained plasma by blowing a small amount (i.e. at a flow rate of 1–5 ml/minute of air at a low pressure through the cartridge). Following treatment of the plasma by dehydration through the cartridge the second blood bag was then placed in a −80° C. freezer to achieve rapid freezing of the dehydrated plasma. After remaining frozen at least overnight, the frozen blood bag was slow thawed in a 4° C. circulating water bath. After thawing was complete, the cryoprecipitate was obvious as a fine white precipitate which was harvested by centrifuging the bag. Alternatively, the entire contents of the bag can be transferred to a centrifuge bottle for the harvesting step or the precipitate can be captured by filtration. Following centrifugation the supernatant is removed by aspiration. The carry-over of supernatant blood proteins can be limited by gently rinsing the inside of the bag/bottle and the surface of the cryoprecipitate pellet with cold isotonic saline.

The cryoprecipitate can then be reconstituted by being dissolved in any of a number or physiologically acceptable solutions such as pure, pyrogen-free water, normal saline, citrated saline, Tris buffer at around pH 7.0, or other solutions well known in the art. The concentration of AHF or Factor VIII is controlled by the volume of liquid used to reconstitute the cryoprecipitate. The method of the present invention recovers about twice as much protein as the usual method for approximately a 100% improvement. The cryoprecipitate contains other proteins besides Factor VIII. In particular the cryoprecipitate usually contains fibrinogen and fibronectin. It may be advantageous to remove these by heat denaturation (i.e., U.S. Pat. No. 4,305,871) or other methods well known in the art; however, these proteins may be used to make "fibrin glue" or "fibrin sealant," which are valuable to control local bleeding during surgery. If desired the Factor VIII produced by redissolving the cryoprecipitate may be subjected to other well known purification techniques to reach even higher levels of purity, but such steps are generally not needed.

EXAMPLE 2

The other clotting factors that do not form a cryoprecipitate can be very important. Of particular interest are Factors II, VII, IX, and X, manufactured in the liver and forming the so-called prothrombin complex. While this material can be used to treat Hemophilia B (Facto IX deficiency), it is most valuable in the treatment of uncontrolled bleeding related to advanced liver disease (e.g., peptic ulcer and esophageal varices). A surprising number of liver disease patients require surgical procedures which render them susceptible to uncontrolled bleeding. If the prothrombin complex can be captured, it will represent an additional product to underwrite the production of the AHF. Since many liver disease patients will ultimately undergo transplant surgery with the concomitant use of immunosuppressive drugs, it is important to avoid exposing these patients to a wide range of viruses as may be present in pooled blood products. The present invention is designed to process single units of blood from known donors so that prothrombin complex is more likely to be disease free. In addition, since the present invention permits the production of cryoprecipitate from nonfrozen plasma, prothrombin complex produced according to the present invention without freezing is less likely to be thrombogenic because freezing tends to activate the material.

To produce prothrombin complex with the present invention one merely replaces the Sephadex with DEAE (diethyl aminoethyl) Sephadex, a material which is useful for ion exchange chromatography as well as for dehydration. It is known that ion exchange materials like DEAE Sephadex have an unusual affinity for proteins of the prothrombin complex. All that is necessary is to make certain that sufficient ion exchange capacity is present to absorb a majority of the prothrombin complex present in a unit of plasma.

Generally the amount of DEAE Sephadex needed to absorb the prothrombin complex is less than the amount needed for optimal dehydration; therefore, it is advantageous to add additional Sephadex, preferably regular Sephadex, which is more economical and its use is preferred. An additional reason to add regular Sephadex is that the DEAE Sephadex binds protein as it dehydrates. The net result can be that although the volume of plasma is substantially reduced, the soluble protein concentration remains the same so that there is no improvement in cryoprecipitate yield. The addition of regular Sephadex (i.e., G-75) results in the additional dehydration needed to improve cryoprecipitate yield. Furthermore, to obtain optimal protein binding to the DEAE Sephadex it may be desirable to have that material prehydrated or preswelled, in which case the DEAE causes little or no dehydration and addition of regular Sephadex is absolutely essential. Following dehydration of the plasma as detailed above, the cartridge 10 is removed from the system, rinsed with a few column volumes of saline buffer (i.e., 0.8% sodium chloride in 0.02M Tris buffer, pH 6.9) to remove contaminating proteins. The first column volume of wash can be retained and pooled with the material in the second blood bag 28.

Following g the saline rinse of the cartridge 10, the prothrombin complex is eluted by flowing 0.5M sodium chloride (buffered with Tris as in the case of saline buffer). Generally, the majority of the prothrombin complex is eluted in the first few milliliters to flow through the cartridge. Of course, gradient elution, as is well known in the art of chromatography, may be used to obtain improved purification. The eluted complex can also be further purified by various other biochemical techniques well known in the art.

Normally, the material will diluted to isotonicity with water or buffer, or it can be dialyzed into physiological saline. The degree of final dilution will depend on the desired strength of the final product. Stability of the complex can be enhanced by adding between 1 and 5% sterilized human serum albumin.

EXAMPLE 3

Instead of the cartridge 10, the dehydrating material of the present invention can be incorporated directly into the blood bag with a resulting decrease in the volume of discarded material. Although it is possible to include loose Sephadex within the second blood bag 28, there may be problems in removing the Sephadex from the dehydrated plasma. Generally, centrifugation cannot effectively pellet the Sephadex. However, a small filter plug of glass wool, PVAA (polyvinyl alcohol-acetate sponge) or similar materials can be included within the outlet 16 to capture the Sephadex and prevent it from contaminating the cryoprecipitate or the Loose Sephadex can be conveniently captured by a downstream filter cartridge (prior to the production of cryoprecipitate). If loose DEAE Sephadex is used, the down stream filter can then serve as the column for the elution of the DEAE Sephadex. Alternatively, the DEAE Sephadex can be placed in the downstream filter cartridge. An additional option is to enclose the dehydrating Sephadex material in a permeable enclosure such as a bag of nylon mesh or similar material. These approaches produce a special blood bag 32 either with loose Sephadex or with an enclosed Sephadex packet 34. It is also possible to construct the packet 34 from a differentially permeable membrane such as dialysis tubing. This allows the use of general purpose dehydrating agents (i.e., Aquacides); however, this approach generally results in much slower dehydration than use of a chromatographic material either loose in the blood bag or enclosed in a fully permeable packet 34. The combination bag-packet may be used with a cartridge-filter 10 set up as explained above.

In using this device after the unit of plasma is dispensed into the bag 32, the plasma filled bag 32 is placed on a rocking or rotary mixer to circulate the enclosed plasma while dehydration takes place. Because there may not be such intimate contact between the plasma and the Sephadex as in the case of the cartridge, the dehydration process may take slightly longer. Following dehydration the plasma may be chilled or frozen in situ or may be transferred to another blood bag prior to the cold precipitation step.

The yields may be slightly lower with the use of the packet 34 because it is generally not possible to remove as much retained plasma from the packet 34 as from the cartridge-filter 10. Also, this embodiment is not as convenient to use with DEAE Sephadex in the packet 34 for production of prothrombin complex. This is because the blood bag 32 must be cut open to get at the packet 34 for elution purposes. This is also somewhat of a safety hazard because it increases the possibility of contact with potentially contaminated plasma. Good results can be obtained by merely inserting the packet 34 into an empty wide column 36 as shown in FIG. 4, or else the packet 34 can be opened and the contents poured into a column, as is well-known in the art. The packet 34 can be readily pressed into the column 36 and a top 38 inserted. At this juncture the packet can be rinsed and eluted exactly like the cartridge-filter 10 in Example 2.

Alternatively, a somewhat poorer yield of prothrombin complex can be obtained by eluting the packet 34 in situ within the blood bag 32. In this case the required volume of eluting buffer is dispensed into the blood bag 32 and the bag placed on a mixer. Elution in this case requires a considerably longer time and is best repeated with both volumes of eluate subsequently pooled. This process may require additional manipulation to dehydrate this increased volume to bring the prothrombin complex to the desired level of potency.

For experimental purposes in assessing the method the loose Sephadex approach can be modeled by simply mixing various volumes of Sephadex into aliquots of plasma. In this experiment 2.0, 1.5, 1.0 of 0.5 grams of dry Sephadex G-75 were dispersed into 25 ml volumes of human plasma. The dispersed Sephadex was mixed well and then incubated for one hour at room temperature to allow the G-75 to swell completely. The Sephadex was filtered from each sample, and a 5 ml portion of each sample was stored at 5° C. for 24 hours. During this time a cryoprecipitate formed which was harvested by centrifugation at 2,000 RPM for 5 min. The volume of the precipitate was measured and harvested. The supernatant was frozen at −70° C. for 2 hours and then thawed at 5° C. for 24 hours, yielding a second cryoprecipitate which was also harvested by centrifugation. Table 2 compares the yields of cryoprecipitate according to amount of Sephadex G-75.

TABLE 2

| Amount of Sephadex | 5° C. Cryoprecipitate | Freeze/thaw Cryoprecipitate | Total Cryoprecipitate |
| --- | --- | --- | --- |
| 2.0 g | 1.2 ml | 2.0 ml | 3.2 ml |
| 1.5 g | 0.6 ml | 1.2 ml | 1.8 ml |
| 1.0 g | 0.3 ml | 0.6 ml | 0.9 ml |
| 0.5 g | 0.1 ml | 0.3 ml | 0.4 ml |

From these results it can be seen that the increase in cryoprecipitate yield is not linear as a function of amount of added Sephadex. Increasing the Sephadex from 0.5 g to 1.0 g (a 100% increase in Sephadex) results in a 125% increase in cryoprecipitate. Increasing Sephadex from 1.5 g to 2.0 g (a 33% increase in Sephadex) results in a further 75% increase in cryoprecipitate (this would scale to 225% yield overall). As the plasma becomes more concentrated, it yields a progressively larger amount of cryoprecipitate. If excessive amounts of Sephadex are added, there is some danger of lowering the quality of the cryoprecipitate as other plasma proteins (besides the coagulation factors) increasingly precipitate. Probably a rate of about 1 g Sephadex per 10 ml of plasma is nearly optimal.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A process for producing purified proteins from plasma by cold precipitation without addition of hydrophilic additives comprising the steps of:

contacting the plasma with a quantity of chromatographic gel, the gel sufficiently unswollen to reduce volume of the plasma by absorbing water therefrom;

removing water from the plasma by allowing the gel to swell;

maintaining intimate contact between the plasma and the chromatographic gel for a sufficient time for water absorption by the gel to be substantially complete;

removing the gel from contact with the plasma;

chilling the plasma to a sufficiently low temperature for a protein precipitate to form;

separating the protein precipitate from liquid plasma; and redissolving the precipitate to produce a purified protein solution.

2. The method of claim 1, wherein the steps of contacting the plasma with a chromatographic gel and maintaining the contact are accomplished by flowing the plasma through a cartridge containing said chromatographic gel.

3. The method of claim 1, wherein the steps of contacting the plasma with a chromatographic gel and maintaining the contact are accomplished by adding the loose chromatographic gel to a container holding the plasma and agitating the container to maintain contact between said gel and the plasma.

4. The method of claim 3, wherein the container is a blood bag to which said gel has been added prior to introduction of the plasma.

5. The method of claim 3, wherein the step of removing the gel from contact with the plasma is accomplished by centrifugation.

6. The method of claim 3, wherein the step of removing the gel from contact with the plasma is accomplished by filtration.

7. The method of claim 1, wherein the plasma is chilled to about 4° C. and the protein precipitate is then separated from the plasma.

8. The method of claim 7, wherein the plasma is frozen following removal of the protein precipitate and is then thawed at 4° C. to yield a second protein precipitate.

9. The method of claim 1, wherein the plasma is chilled below 4° C. until frozen solid and is then thawed at 4° C. to yield the protein precipitate.

10. The method of claim 1, wherein the chromatographic gel is Sephadex brand cross-linked dextran.

11. The method of claim 10, wherein the Sephadex brand cross-linked dextran contains ion exchange groups that bind prothrombin complex and wherein the method further comprises the step of eluting the cross-linked dextran containing ion exchange groups to release purified prothrombin complex.

12. A process for producing purified proteins from individual units of plasma by cold precipitation without addition of hydrophilic additives comprising the steps of:

contacting an individual unit of plasma with a quantity of insoluble water-absorbing material sufficient to reduce volume of the unit of plasma by absorbing water therefrom;

removing water from the plasma by allowing the insoluble water-absorbing material to absorb the water;

maintaining intimate contact between the unit of plasma and the insoluble water-absorbing material for a sufficient time for water absorption by the water-absorbing material to be substantially complete;

removing the water-absorbing material from contact with the unit of plasma;

chilling the unit of plasma to a sufficiently low temperature for a protein precipitate to form;

separating the protein precipitate from liquid plasma; and redissolving the precipitate to produce a purified protein solution.

13. A process for producing purified proteins from plasma by cold precipitation of a single unit of donor plasma without addition of hydrophilic additives comprising the steps of:

contacting a single unit of plasma from one donor with a quantity of chromatographic gel, the gel sufficiently unswollen to reduce volume of the plasma by absorbing water therefrom;

removing water from the single unit of plasma by allowing the gel to swell;

maintaining intimate contact between the single unit of plasma and the chromatographic gel for a sufficient time for water absorption by the gel to be substantially complete;

removing the gel from contact with the single unit of plasma;

chilling the single unit of plasma to a sufficiently low temperature for a protein precipitate to form;

separating the protein precipitate from liquid plasma; and redissolving the precipitate to produce a purified protein solution derived from a single donor.

* * * * *